United States Patent [19]

Lantero, Jr.

[11] 4,355,105
[45] Oct. 19, 1982

[54] GLUTARALDEHYDE/POLYETHYLENIMINE IMMOBILIZATION OF WHOLE MICROBIAL CELLS

[75] Inventor: Oreste J. Lantero, Jr., Goshen, Ind.

[73] Assignee: Miles Laboratories, Inc., Elkhart, Ind.

[21] Appl. No.: 248,718

[22] Filed: Mar. 30, 1981

[51] Int. Cl.$^3$ .................. C12P 19/24; C12N 11/00; C12N 9/90; C12N 9/92
[52] U.S. Cl. .................. 435/94; 435/174; 435/177; 435/233; 435/234
[58] Field of Search .......... 435/174, 177, 180, 94, 435/233, 234, 170

[56] References Cited

U.S. PATENT DOCUMENTS 3,779,869 12/1973 Zienty ........................ 435/174
3,989,597 11/1976 Lee et al. .................... 435/174
4,212,943 7/1980 Borglum ...................... 435/180
4,288,552 9/1981 Gestrelius .................... 435/174

FOREIGN PATENT DOCUMENTS 1099 1/1979 European Pat. Off. .
2019410 10/1979 United Kingdom .

Primary Examiner—David M. Naff
Attorney, Agent, or Firm—Jerome L. Jeffers

[57] ABSTRACT

Whole microbial cells containing enzymes not sensitive to glutaraldehyde such as sucrose mutase or glucose isomerase are immobilized by forming a reaction product of the cells in an aqueous medium with glutaraldehyde, reacting the reaction product with polyethylenimine to flocculate the reaction product, and recovering the flocculated reaction product from the aqueous medium. Reacting the cells with glutaraldehyde prior to reacting with polyethylenimine results in flocculated cells that can be more easily separated from the aqueous medium.

8 Claims, No Drawings

GLUTARALDEHYDE/POLYETHYLENIMINE IMMOBILIZATION OF WHOLE MICROBIAL CELLS

The use of enzymes derived from microbial cells to effect specific chemical transformations is well known. The free cells can be used efficiently in a batch-type process but do not lend themselves to continuous, industrial scale processes. This difficulty has led to increased interest in the preparation of various forms of immobilized biocatalysts.

A large number of immobilization techniques have been disclosed in the literature. British Patent Application No. 2,019,410 filed Apr. 18, 1979 by Novo Industri A.S. discloses a process for immobilizing certain biocatalysts by reacting, in an aqueous medium, microbial cells with glutaraldehyde in the presence of a polyamine with a significant content of primary amino groups and isolating the immobilized biocatalyst. In a typical example a fermentation broth of *Bacillus pasteuri* is treated with polyethylenimine to flocculate the cells and the polymer is then crosslinked with glutaraldehyde to provide a reaction product which can be recovered by filtration, dried and used in a continuous biocatalytic process. The disclosure of this patent calls for the addition of polyethylenimine to the fermentation beer before introducing the glutaraldehyde. This is necessary because the system is designed for the immobilization of microorganisms whose enzymes are sensitive to glutaraldehyde and the PEI pretreatment is said to prevent the inactivation of the enzyme by glutaraldehyde.

However, many enzymes, such as glucose isomerase and sucrose mutase, are not sensitive to glutaraldehyde and can, therefore, be contacted with this material without being pretreated. It has been discovered that when immobilizing those microorganisms whose enzymes are not sensitive to glutaraldehyde, it is desirable to introduce glutaraldehyde before PEI because this results in an immobilized microorganism which can be recovered from the fermentation broth much more readily than is the case with the PEI pretreatment disclosed in the aforementioned British patent.

The biocatalytic conversion of sucrose to palatinose with subsequent hydrogenation of palatinose to palatinit, a noncaloric sweetner, is known. The biocatalytic conversion can be accomplished by contacting viable cells of *Protaminobacter rubrum* containing sucrose-mutase activity with a sucrose containing medium. This conversion is carried out in a batchtype process, the economics of which would be improved by the immobilization of the biocatalyst to form particles possessing physical characteristics which would render it suitable for use in a packed-bed reactor in which the particles retain their biocatalytic activity during a continuous flow conversion of sucrose to palatinose.

The stabilization of microorganisms exhibiting biocatalytic activity of the use of a cationic flocculating agent and a crosslinking agent is known. U.S. Pat. No. 4,212,943 (issued July 15, 1980) discloses a process for the production of an aggregate of bacterial cells having improved hardness which process involves the use of a crosslinked reaction product of glutaraldehyde and/or cyanuric halide and a particular epihalohydrin-polyamine copolymer. A strain of *Streptomyces olivaceus* is disclosed as being the preferred species of microorganism for immobilization by this technique.

Copending application Ser. No. 156,496 (filed June 4, 1980) discloses the immobilization of a culture of *Bacillus licheniformis* by forming a reaction product of the microorganism with glutaraldehyde and polyethylenimine.

The prior art does not disclose the immobilization of *Protaminobacter rubrum* or the use of the immobilized microorganism in the continuous conversion of sucrose to palatinose.

SUMMARY OF THE INVENTION

The present invention involves a method for the immobilization of an enzyme producing microorganism whose enzyme is not sensitive to glutaraldehyde which method comprises the steps of:
 (a) providing an aqueous medium containing whole cells of the microorganism;
 (b) adding glutaraldehyde to the aqueous medium to form a reaction product with the microorganism;
 (c) adding polyethylenimine to the aqueous medium to flocculate the reaction product; and
 (d) recovering the flocculated reaction product from the aqueous medium.

DETAILED DESCRIPTION

The immobilization technique of the present invention is carried out by first adding glutaraldehyde to the aqueous medium containing the microorganism to form a reaction product which is then flocculated by the addition of polyethylenimine. The flocculated reaction product is removed from the aqueous medium, dried and used in a continuous operation for converting a particular organic material to another by biocatalytic means. The selection of a particular polyethylenimine is not critical although those polymers having a molecular weight within the range of from 1,800 to 60,000 are preferred. Typically the mole ratio of gluaraldehyde to polyethylenimine on the monomer will range from 3.9:1 to 0.4:1. The weight ratio of the combination of glutaraldehyde and polyethylenimine to the dry weight of the microorganism cells will typically range from 0.20:1 to 0.7:1.

The method of practicing the present invention is further illustrated by the following examples in which the polyethylenimine was a polymeric form of ethylenimine obtained from Eastman Kodak Co. at a 50% aqueous solution.

EXAMPLE 1

In this example *Protaminobacter rubrum* was produced by inoculating a medium consisting of sugar beet thick juice, dibasic ammonium phosphate and filtered corn steep liquor with a phage resistant mutant from a strain of *P. rubrum* deposited at the Official European Centraalbureau Voor Schimmelcultures in Barn, Netherlands under deposit No. CBS 574.77. Prior to immobilization, the fermentation beer was concentrated approximately ten-fold by centrifugation. Whole cell immobilization was conducted in the following manner, at room temperature except where noted.

A. 0.5% GA, PEI Treatment 500 ml. of cell slurry concentrate was adjusted to pH 7.0 with 2 N NaOH; 10% (v/v) glutaraldehyde (GA) solution was slowly added to the cell slurry while stirring to reach a concentration of 0.5% by volume (25 ml.). During the GA addition, the pH was kept at 7.0 by careful addition of 2 N NaOH. One hour after the GA addition, two volumes of deionized water (1000 ml.)

were added to the slurry. Then, while mixing, a 5% (w/v) solution of PEI was slowly added until maximum flocculation appeared to take place (22 ml.). The cell mass was collected by low speed centrifugation, and the resulting pellet was further dewatered by filtration on a Buchner funnel. The cell cake was washed with water and extruded through a 1.1-1.5 mm. orifice by means of a syringe. The material was allowed to air dry at room temperature for 24 hours. A yield of 13.8 g. was obtained.

B. 0.1% GA, PEI Treatment 500 ml. of the cell slurry concentrate used in A was adjusted to pH 7.0, and treated with GA as in A. In this experiment, the final GA concentrate was reduced to 0.1% by volume (5 ml. of 10% GA). After one hour, the slurry was diluted with two volumes of deionized water (1000 ml.), and then treated with PEI as above to obtain maximum flocculation (25 ml. of 5% PEI). The cell mass was recovered by centrifugation as above, and the pellet was then extruded. After air drying, to yield of 12.6 g. of material was obtained, with an activity of 330 units/g. for 16/25 mesh particles.

C. 0.2% GA, PEI Treatment 775 ml. of cell slurry concentrate was adjusted to pH 7.0 and treated with GA at a concentration of 0.2% (v/v) by addition of 15.5 ml. of 10% GA. After the GA addition, the cell slurry was diluted with two volumes of deionized water and cell mass fluocculated by addition of PEI (33.5 ml. of 5% PEI). The cell mass was collected on a Buchner funnel and washed with deionized water. Filtration was quite rapid. The washed cake was then extruded and air dried. A yield of 21.6 g. was obtained. The activity of 16/25 mesh particles was estimated at 299 units/g.

D. 15% GA, PEI, 0.05% GA Treatment 2600 ml. of cell slurry concentrate was adjusted to pH 7.0. GA was then added (39.0 ml. of 10% GA) to obtain. 15% (v/v). After GA addition, two volumes (5600 ml.) of deionized water were added. The cell mass was then flocculated by addition of 5% PEI, 120 ml. of PEI solution appeared to cause maximum flocculation. The flocculated material was allowed to settle for one hour and supernatant was then siphoned off (approximately half the volume). The cell mass could not be collected by filtration because of extremely slow filtration rate. The cell mass was then diluted with water to the original volume prior to siphoning, and more PEI was added (50 ml. of 5%) followed by addition of 12 ml. of 10% GA (total GA 0.2%). After standing 1.5 hours, the clear liquid above the settled cell mass was siphoned off. Again, an attempt was made to collect the cell mass by filtration on a Buchner funnel. This time filtration was very rapid. The resulting cell cake was washed with water, extruded, and air dried. A yield of 80.7 g. of material was obtained and resulted in an activity of 256 units/g. for 16/25 mesh particles.

E. Low Temperature 0.2% GA, PEI Treatment 1500 ml. of cell slurry concentrate (83 units/ml. of slurry) was adjusted to pH 7.0 and then placed in an ice bath. When the temperature of the slurry reached 4° C., GA was added (30 ml. of 10% GA) to reach 0.2% v/v. After GA addition, the slurry was diluted with three volumes of deionized water (25° C., 4500 ml.). The cells were then flocculated by addition of 30 ml. of 5% w/v PEI. The cell mass was allowed to settle for one hour. The clear supernatant was siphoned off (above 50% of total volume). The cells were collected on a Buchner funnel, washed, extruded, and dried at room temperature as above. A total of 31.8 g. of dried material was obtained which possessed 511 units/g. for 16/25 mesh particles.

The sucrose-mutase activity of the immobilized whole cells was determined by assaying particles of a specified size in the recirculation differential reactor (RDR) (Ford et al; "Recirculation Reactor System for Kinetic Studies of Immobilized Enzymes", in Enzyme Engineering. Wingard, L. B., Jr.; Ed., Interscience Publishers, New York, 1972, pp. 267-284). The essential parts of the RDR system are the differential packed bed reactor, a temperature controlled water bath, a feed reservoir, and a peristaltic pump appropriately connected.

The assay is conducted by placing a known amount of fully hydrated immobilized enzyme in the column, (usually less than a gram) the column is then immersed in the bath and washed with an appropriate buffer. A known amount of substrate is placed in the reservoir and immersed in the bath. After a period of time for thermal equilibration, the assay is started by pumping the substrate through the bed. At desired time intervals a small amount of substrate is removed from the reservoir and, by an appropriate method, the amount of product formed is estimated in the samples removed from the reservoir. By knowing the amount of product formed at the various reaction times the initial velocity of enzyme reaction can be obtained.

The conversion of sucrose to palatinose by whole cell immobilized sucrose-mutase was examined by the use of an integral column reactor. Integral column reactors involve percolating the substate through the enzyme bed at a desired temperature at specific flow rates, and observing the resulting conversion. The reaction time would be inversely related to substrate flow rate. The integral column reactor can be very sensitive to mass transport control of the reaction: namely external and internal diffusion.

External diffusion control can be overcome by increased substrate linear velocities; this requires an enzyme bed of sufficient depth to obtain the necessary reaction time. In general, to reduce the influence of diffusion, conditions are used to improve increased expression of enzyme activity such that the reaction rate is more under kinetic control and less under diffusion control. Altering temperature and pH can effectively reduce enzyme activity to limit diffusion influences; however, caution is required so as not to radically decrease the stability of the enzyme.

Altering the immobilized enzyme particle by reducing the particle size or altering the immobilization process to decrease the specific activity (units/g. of immobilized) are other means of reducing the influence of mass transport effects. Particle size and specific activity of the immobilized enzyme are key parameters which govern the reactor design needed to carry out the desired conversion.

The integral reactor system consisted of a 1.5 × 100 cm. glass jacketed column. The temperature of the column was maintained at 30° C. by an external constant temperature water bath. To control flow rate, a peristaltic pump was used to control the column effluent. In all cases, the columns were operated in the downflow mode.

Prior to adding enzyme to the column, a glass wool plug was put on the column end plate. Five (5) ml. of coarse alumina was placed on top of the glass wool. A slurry of fully hydrated immobilized enzyme was then poured onto the alumina bed. After the enzyme settled, substrate was allowed to percolate downward through the bed.

Substrates for the experiment were prepared by using table grade sugar (Domino) prepared in 5 mM phosphate buffer at pH 7.0.

The amount of palatinose formed was determined by HPLC of samples obtained at various reaction times. The results of using a typical sample of *P. rubrum* immobilized by the technique of this example are set out in Table I.

TABLE I

| Enzyme | 10 g., PEI-GA, 16/25 mesh |
|---|---|
| Reactor | Intergral Column |
| Substrate | 48% w/w Sucrose, 5 mM phosphate pH 7.0 |
| Temperature | 30° C. |

| Nominal Flow Rate (ml./hr) | Normalized Reaction Time (Min.) | HPLC Sugar Profile | | | | |
|---|---|---|---|---|---|---|
| | | F | G | S | P | 1,1' |
| 146 | 16.38 | 0.8 | 0.2 | 85.7 | 12.3 | 1.0 |
| 124 | 19.06 | 0.8 | 0 | 83.8 | 14.1 | 1.3 |
| 96 | 24.86 | 1.5 | 0.5 | 77.6 | 18.2 | 2.2 |
| 47 | 51.07 | 2.5 | 1.4 | 58.9 | 34.0 | 3.2 |
| 38 | 62.31 | 2.4 | 1.4 | 50.3 | 41.1 | 4.8 |
| 25 | 96.21 | 2.9 | 1.3 | 35.9 | 53.4 | 6.5 |
| 25 | 96.59 | 3.1 | 1.2 | 36.3 | 52.8 | 6.6 |
| 19.3 | 122.89 | 3.3 | 1.7 | 27.1 | 59.8 | 8.1 |
| 14.5 | 164.30 | 4.1 | 2.0 | 17.6 | 66.9 | 9.4 |
| 9.9 | 239.35 | 4.6 | 2.3 | 8.9 | 72.0 | 12.2 |
| 6.8 | 348.96 | 5.2 | 2.7 | 4.3 | 74.6 | 13.2 |
| 4.9 | 481.30 | 6.8 | 3.9 | 0.6 | 72.9 | 15.7 |
| 4.3 | 549.48 | 6.8 | 3.4 | 0.7 | 72.0 | 17.1 |
| 4.0 | 585.70 | 6.7 | 3.4 | 0.5 | 72.0 | 17.4 |
| 3.6 | 652.23 | 7.3 | 3.7 | 0 | 70.0 | 19.0 |

F - fructose
G - glucose
P - palatinose
S - sucrose
1,1' - 1,1' isomer

EXAMPLE II

Immobilization of *S. Olivaceus* Mutant by GA-PEI Process

Whole beer from the combination of two 10 liter fermentations of *S. olivaceus* was used for immobilization. The cells from two liters of the whole beer were collected by centrifugation and suspended in deionized water to a final volume of 1000 ml. Two 500 ml. portions of the cell slurry were treated in the following manner:

A. 0.25% GA-PEL.

1. Add 12.5 ml. of 10% (v/v) glutaraldehyde (GA) and let stand one hour at pH 6.55.
2. Dilute the cell slurry by the addition of 1000 ml. of deionized water.
3. Add 8.4 ml. of 2.5% (w/v) PEI to flocculate the cells.
4. Collect the cell mass by filtration on a Buchner funnel and wash the cell cake with water.
5. By means of a 10 ml. syringe extrude the cell cake through an opening of approximately 1.5 mm.
6. Dry for 15 hours at 60° C. to obtain 8.2 g. of material.

B. 0.4% GA-PEI.

1. To 500 ml. of cell slurry is added 20 ml. of 10% (v/v) GA and combination is allowed to stand for one hour at pH 6.6.

2. The immobilization process was carrid out as above with the recovery of 8.5 g. of dried extruded material.

C. PEI-0.12% - GA -PEI.

The above-described process of immobilizing the microorganism was modified whereby the PEI was added prior to and after the GA treatment. The following procedure describes the process using the same *S. olivaceus* fermentation broth.

1. To 1000 ml. of whole beer add 2000 ml. of deionized water.
2. Add 16.2 ml. of 5% (w/v) PEI to obtain flocculation.
3. Adjust pH of slurry from 5.79 to 7.50 with 2 N sodium hydroxide.
4. Add 35 ml. of 10% (v/v) GA and let stand one-half hour at which point pH dropped to 7.25. At this point, filtration could not be accomplished.
5. Add 5% (w/v) PEI to obtain apparent maximum flocculation, 27.8 ml.
6. After standing for one hour the cell mass was collected by filtration on a Buchner funnel, and it was noted at this point that filtration was extremely rapid.
7. The cell cake was washed with water.
8. The cell cake was so dry that it was very difficult to extrude by the syringe method, so the whole cell cake was dried resulting in 10.9 g. of material.

The glucose isomerase activity of the immobilized samples was estimated at 70° C. using a batch assay technique using small particles ($\approx 80$ mesh). The assay was carried out in 125 ml. Erlenmeyer flasks in which the dry enzyme was hydrated in substrate (1 M glucose, 0.1 M Tris, 0.1 M maleic acid, 4.1 mM $MgSO_4.7H_2O$ and 5 mmM $NaHSO_4$ at pH 8.0) for 10 minutes at room temperature. The assay reaction was started by placing the flask in a 70° C. shaker water bath. At 15, 30, 45, 60 and 75 minutes, a 0.05 ml. sample of the reaction mixture was removed and added to 1.0 ml. of 0.1M $HClO_4$ solution to stop the reaction. The amount of fructose formed in each sample was then estimated by the cysteine $H_2SO_4$ method. The activity was calculated through regression analysis of fructose formed with respect to time, where a unit of activity represents one $\mu$ mole of fructose formed per minute under conditions of the assay.

| Glucose Isomerase Activity of Immobilized *S. Olivaceus* | |
|---|---|
| Preparation | Activity (units/g.) |
| A. .25% GA—PEI | 118[a] |
| B. .4% GA—PEI | 65.1[a] |
| C. PEI—.12%-GA—PEI | 192[b] |

[a]Substrate made up with 1M glucose, .1M Tris, .1M maleic acid, .02M $M_gSO_4.7H_2O$ and 5mM $NaHSO_3$, H 8.0
[b]Substrate contained 30% w/v cerelose 4.1mM $M_gSO_4.7H_2O$ and 4.1mM $NaHSO_3$ at pH 7.5.

Although the activity results cannot be compared exactly, because the assay varied in substrate composition, it can be stated that all the preparations are active even in the absence of cobalt ions.

EXAMPLE III

Immobilization of *B. Licheniformis* Mutant by GA-PEI Process

The following example illustrates the GA-PEI process for preparing immobilized *B. licheniformis* whole cell glucose isomerase. Fermentation broth from a 300 gallon fermentation of the mutant was used.

A. 0.25% GA-PEI.

1. 3800 ml. of whole beer was adjusted from pH 7.2 to 8.0 with 2 N N₂OH.

2. Add 95 ml. of 10% (v/v) GA, maintained at pH 8.0.

3. After standing for approximately one-half hour, 200 ml. of 5% PEI was added which appeared to completely flocculate the cell mass.

4. After standing for one hour, approximately 75% of the supernatant was decanted and the cell mass recovered by filtration on a Buchner funnel.

5. The cell cake was washed with about 500 ml. of water and then dried at 60° C. for about 15 hours. A total of 44.0 g. of the dried material was obtained.

B. 0.4% GA-PEI.

1. 3800 ml. of whole beer was adjusted to pH 8.0 and cooled to 6° C.

2. 152 ml. of 10% (v/v) Ga was added; the pH remained at 8.0.

3. After standing for 15 minutes the cell material was flocculated by the addition of 5% (w/v) PEI.

4. A total of 80.6 g. of material was recovered.

C. 0.25% GA-PEI.

1. 1000 ml. of whole beer was adjusted to pH 8.0 at room temperature.

2. 25 ml. of 10% (v/v) GA was added while maintaining the pH at 8.0.

3. After about 15 minutes, the cell slurry was diluted by the addition of 2000 ml. of deionized water prior to flocculation.

4. The cell flocculation was completed by the addition of 50 ml. of 5% (w/v) PEI.

5. The cell mass settled very rapidly and approximately 75% of the volume was decanted prior to recovery of the cell mass by filtration on a Buchner funnel.

6. The washed cell cake was extruded by means of a 10 ml. syringe.

7. The extruded material was dried at 60° C. for about 15 hours resulting in a recovery of 13.5 g. of material.

the glucose isomerase activity of the immobilized samples was estimated by using a recirculation differential reactor as described. The temperature of the assay was at 70° C. using as substrate 2 M glucose containing 4.1 mM $M_gSO_4.7H_2O$, 0.5 mM $CoCl_2.6H_2O$ and 20 mM Hepes adjusted to pH 7.4. The amount of fructose found was determined by the cysteine—$H_2SO_4$ method. A unit of activity is the same as described above for *S. olivaceus* immobilized GI assay.

| Activity of Immobilized *B. Licheniformis* Glucose Isomerase | |
|---|---|
| Immobilized Enzyme | Activity (units/gm) |
| A. 0.25% GA—PEI | 87.7 |
| B. 0.4% GA—PEI | 69.7 |

| -continued | |
|---|---|
| Activity of Immobilized *B. Licheniformis* Glucose Isomerase | |
| Immobilized Enzyme | Activity (units/gm) |
| C. 0.25% GA—PEI | 69.8 |

What is claimed is:

1. A method for the immobilization of whole cells of an enzyme producing microorganisms whose enzyme is selected from the group of sucrose mutase and glucose isomerase which method comprises the steps of:
    (a) providing an aqueous medium containing whole cells of the microorganism;
    (b) adding glutaraldehyde to the aqueous medium and allowing sufficient time for the formation of a reaction product between the glutaraldehyde and the microorganism cells; adding polyethylenimine to the aqueous medium said polyethylenimine having a molecular weight within the range of from 1,800 to 60,000 and in sufficient quantity so that the mole ratio of glutaraldehyde to polyethylenimine monomer ranges from 3.9:1 to 0.4:1 and the weight ratio of the combination of glutaraldehyde and polyethylenimine to the dry weight of the cells is within the range of from 0.20:1 to 0.7:1 to flocculate the reaction product; and
    (d) recovering the flocculated reaction product from the aqueous medium by filtration.

2. The method of claim 1 wherein the microorganism is *Protaminobacter rubrum*.

3. The method of claim 1 wherein the microorganism is *S. olivaceus*.

4. The method of claim 1 wherein the microorganism is *B. licheniformis*.

5. A method for converting sucrose to palatinose which comprises contacting the sucrose with the material prepared by the method of claim 2 for a period of time sufficient to cause the desired amount of conversion.

6. A method for the immobilization of whole cells of *Protaminobacter rubrum* which comprises the steps of:
    (a) providing an aqueous medium containing whole cells of the microorganism;
    (b) adding glutaraldehyde to the aqueous medium and allowing sufficient time for the formation of a reaction product between the glutaraldehyde and microorganism;
    (c) adding polyethylenimine having a molecular weight within the range of from 1,800 to 60,000 to the aqueous medium to flocculate the reaction product; and
    (d) recovering the flocculated reaction product from the aqueous medium provided further that the mole ratio of glutaraldehyde to polyethylenimine monomer ranges from 3.9:1 to 0.4:1 and the weight ratio of the combination of glutaraldehyde and polyethylenimine to the dry weight of the cells is within the range of from 0.20:1 to 0.7:1.

7. The product produced by the process of claim 6.

8. A method for converting sucrose to palatinose which comprises contacting the sucrose with the material of claim 7 for a time sufficient to cause the desired amount of conversion.

* * * * *

UNITED STATES PATENT OFFICE
CERTIFICATE OF CORRECTION

PATENT NO. : 4,355,105
DATED : October 19, 1982
INVENTOR(S) : Oreste J. Lantero

It is certified that error appears in the above-identified patent and that said Letters Patent are hereby corrected as shown below:

Column 3, line 35 - change "15%" to ---.15%---.

Column 3, line 38 - change "15%" to ---.15%---.

Column 8, line 18 - insert ---(c)--- between "cells;" and "adding".

Signed and Sealed this

Fifteenth Day of March 1983

[SEAL]

Attest:

Attesting Officer

GERALD J. MOSSINGHOFF

Commissioner of Patents and Trademarks